United States Patent
Courtney et al.

(10) Patent No.: US 9,763,718 B2
(45) Date of Patent: Sep. 19, 2017

(54) BONE SCREW

(71) Applicant: Eminent Spine LLC, Georgetown, TX (US)

(72) Inventors: Steve Courtney, Plano, TX (US); David Freehill, Temple, TX (US)

(73) Assignee: Eminent Spine LLC, Georgetown, TX (US)

( * ) Notice: Subject to any disclaimer, the term of this patent is extended or adjusted under 35 U.S.C. 154(b) by 255 days.

(21) Appl. No.: 13/691,975

(22) Filed: Dec. 3, 2012

(65) Prior Publication Data

US 2013/0096636 A1 Apr. 18, 2013

Related U.S. Application Data

(63) Continuation-in-part of application No. 12/629,585, filed on Dec. 2, 2009, now Pat. No. 8,574,274, which
(Continued)

(51) Int. Cl.
| | |
|---|---|
| *A61B 17/86* | (2006.01) |
| *A61B 17/70* | (2006.01) |
| *A61B 17/80* | (2006.01) |

(52) U.S. Cl.
CPC ...... *A61B 17/8625* (2013.01); *A61B 17/7037* (2013.01); *A61B 17/7059* (2013.01);
(Continued)

(58) Field of Classification Search
CPC ... A61B 17/86; A61B 17/861; A61B 17/8625; A61B 17/7059; A61B 17/8605
(Continued)

(56) References Cited

U.S. PATENT DOCUMENTS

| | | | | |
|---|---|---|---|---|
| 4,241,638 A | * | 12/1980 | Shimizu | F16B 25/0031 411/386 |
| 6,010,503 A | | 1/2000 | Richelsoph et al. | |

(Continued)

FOREIGN PATENT DOCUMENTS

EP 2077396 A1 * 7/2009 ............ F16B 5/0275

OTHER PUBLICATIONS

ISR PCT/2009/066426, Jan. 26, 2010.
ISR PCT/2009/066449, Jan. 26, 2010.
PCT/US2012/067536, Feb. 6, 2013, International Search Report.

*Primary Examiner* — Christopher Beccia
(74) *Attorney, Agent, or Firm* — Scott T. Griggs; Griggs Bergen LLP

(57) ABSTRACT

A bone screw is disclosed. A head includes a driver-receiving element formed thereon. A shank having a proximal portion, which is integrally connected to the head, and a distal portion maintains a constant diameter from the proximal portion to the distal portion. Three helical threads extend around the shank from the proximal portion to the distal portion. The three helical threads are symmetrically and helically aligned and advance uniformly along the length of the shank for each revolution to define a thread depth that remains constant along the length of the shank. The three helical threads respectively include three leads, which are offset by approximately 120° from each another. A tip is integrally connected to the distal portion of the shank and the tip intersects with a flute to define a self-tapping point.

6 Claims, 3 Drawing Sheets

Related U.S. Application Data is a continuation-in-part of application No. 12/629,779, filed on Dec. 2, 2009, now Pat. No. 8,685,069.

(60) Provisional application No. 61/119,312, filed on Dec. 2, 2008, provisional application No. 61/119,324, filed on Dec. 2, 2008, provisional application No. 61/565,881, filed on Dec. 1, 2011.

(52) U.S. Cl.
CPC ........ *A61B 17/809* (2013.01); *A61B 17/8057* (2013.01); *A61B 17/861* (2013.01); *A61B 17/8605* (2013.01)

(58) Field of Classification Search
USPC ........... 606/60, 246–279, 300–331; 411/411, 411/412, 424
See application file for complete search history.

(56) References Cited

U.S. PATENT DOCUMENTS

| | | | |
|---|---|---|---|
| 6,740,086 B2 | 5/2004 | Richelsoph | |
| 6,843,791 B2 | 1/2005 | Serhan | |
| 7,211,086 B2 | 5/2007 | Biedermann et al. | |
| 7,942,907 B2 | 5/2011 | Richelsoph | |
| 8,382,811 B2* | 2/2013 | Crook | A61B 17/7037 411/412 |
| 2002/0143341 A1 | 10/2002 | Biedermann et al. | |
| 2003/0088251 A1* | 5/2003 | Braun | A61B 17/7022 606/263 |
| 2004/0260306 A1 | 12/2004 | Fallin et al. | |
| 2005/0038438 A1* | 2/2005 | Anderson | A61B 17/7071 606/304 |
| 2005/0085913 A1 | 4/2005 | Fraser et al. | |
| 2005/0187552 A1 | 8/2005 | Michelson | |
| 2006/0235400 A1 | 10/2006 | Schneider | |
| 2007/0055240 A1 | 3/2007 | Matthis et al. | |
| 2007/0167949 A1* | 7/2007 | Altarac | A61B 17/7032 606/86 A |
| 2009/0018588 A1 | 1/2009 | Eckhof et al. | |
| 2009/0143824 A1 | 6/2009 | Austin et al. | |
| 2009/0318977 A1 | 12/2009 | Di Giacomo et al. | |
| 2010/0049255 A1 | 2/2010 | Matthis et al. | |
| 2010/0145397 A1* | 6/2010 | Overes | A61B 17/68 606/319 |
| 2010/0152787 A1 | 6/2010 | Walsh et al. | |
| 2010/0198272 A1 | 8/2010 | Keyer et al. | |
| 2010/0262196 A1 | 10/2010 | Barrus et al. | |
| 2010/0312286 A1 | 12/2010 | Dell'Oca | |
| 2011/0054546 A1 | 3/2011 | Abdelgany | |

\* cited by examiner

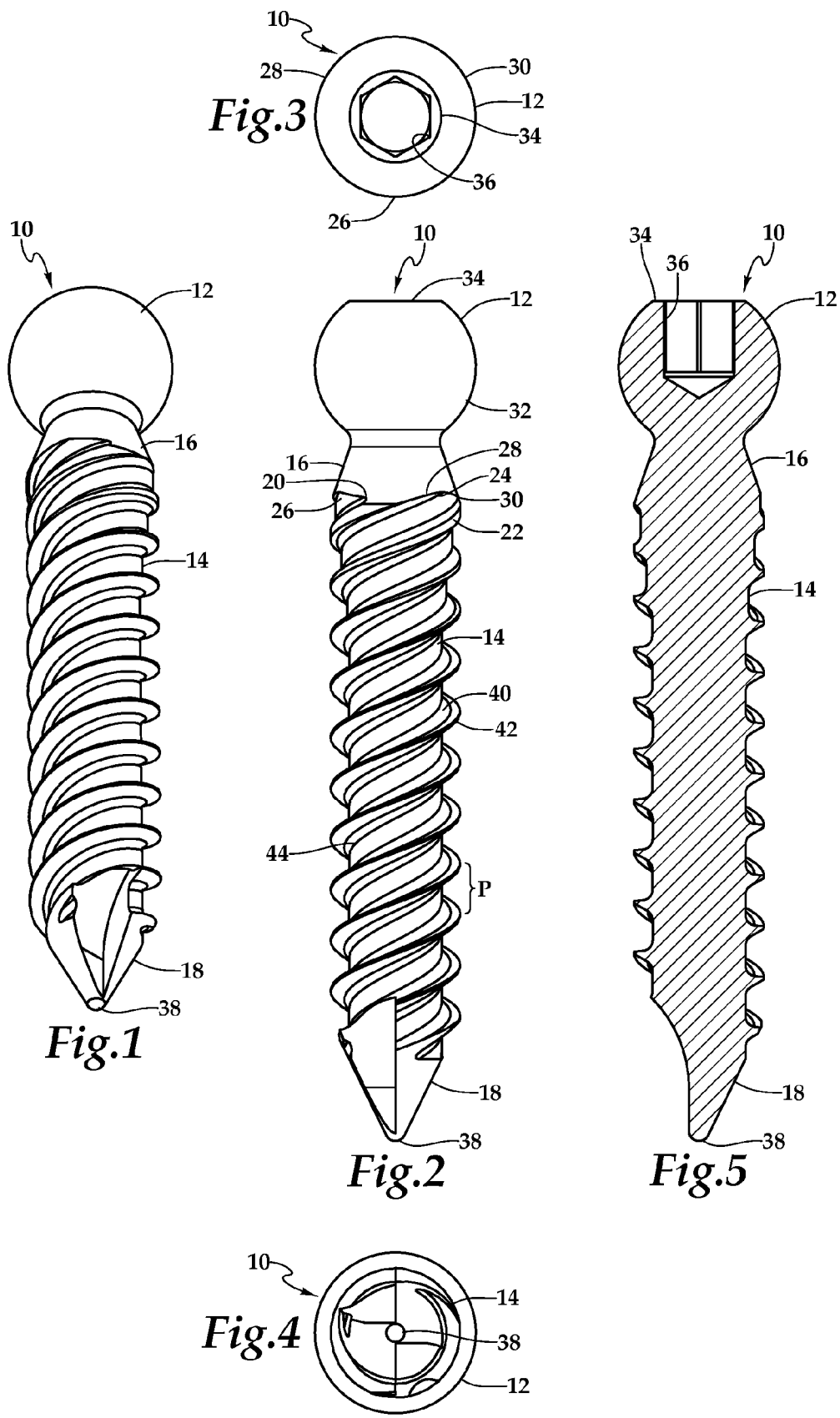

BONE SCREW

PRIORITY STATEMENT & CROSS-REFERENCE TO RELATED APPLICATIONS

This application claims priority from application Ser. No. 61/565,881 entitled "Bone Screw" and filed on Dec. 1, 2011 in the names of Steve Courtney and David Freehill. This application is also a continuation-in-part of co-pending patent application Ser. No. 12/629,585 entitled "Pedicle Screw Fixation System and Method for Use of Same" and filed on Dec. 2, 2009 in the names of Steve Courtney and David Freehill, which claims priority from patent application Ser. No. 61/119,312 entitled "Pedicle Screw Fixation System and Method for Use of Same" and filed on Dec. 2, 2008 in the names of Steve Courtney and David Freehill. This application is also a continuation-in-part of co-pending patent application Ser. No. 12/629,779 entitled "Bone Plate and Plating System for Use of Same" and filed on Dec. 2, 2009 in the names of Steve Courtney and David Freehill, which claims priority from patent application Ser. No. 61/119,324 entitled "Anterior Buttress Staple and Method for Use of Same" and filed on Dec. 2, 2008 in the names of Steve Courtney and David Freehill. All of the above applications are hereby incorporated by reference for all purposes.

TECHNICAL FIELD OF THE INVENTION

This invention relates, in general, to a fastener for the connection of a medical device to bone and, in particular, to a bone screw.

BACKGROUND OF THE INVENTION

Bone screws are used for a variety of surgical purposes, including the immobilization of fractured bone segments to aid in the healing process, and as an adjunct to spine fusion surgery to help hold implants in place. With respect to the later, a need exists for bone screws that furnish improved pull-out strength under axial, distractive, and compressive force loads applied through the patient's natural movement. There is also a need for bone screws with easier implantation and reduced insertion time.

SUMMARY OF THE INVENTION

It would be advantageous to achieve a bone screw that provides improved pull-out strength under the loads applied through the patient's natural movement. It would also be desirable to enable a mechanical solution that would improve insertion as well as removal, including enabling revisions. To better address one or more of these concerns, in one aspect of the invention, a bone screw is disclosed that in one embodiment includes a head having a driver-receiving element formed thereon. A shank is integrally connected to the head and includes a proximal portion and a distal portion such that a constant diameter exists from the proximal portion to the distal portion.

A triple helical thread extends around the shank from the proximal portion to the distal portion. The triple helical thread is defined by first, second, and third helical threads that are symmetrically and helically aligned while advancing uniformly along the length of the shank for each revolution to provide a thread depth that remains constant along the length of the shank. The first, second, and third helical threads respectively include a first lead, a second lead, and a third lead offset by approximately 120° degrees from one another. A tip is integrally connected to the distal portion of the shank and intersected with a flute to define a self-tapping point. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 1 is perspective view of a bone screw according to one embodiment;

FIG. 2 is a front elevation view of the bone screw depicted in FIG. 1;

FIG. 3 is top plan view of the bone screw depicted in FIG. 1;

FIG. 4 is bottom plan view of the bone screw depicted in FIG. 1;

FIG. 5 is a cross-sectional view of the bone screw depicted in FIG. 1;

DETAILED DESCRIPTION OF THE INVENTION

Figure 6:
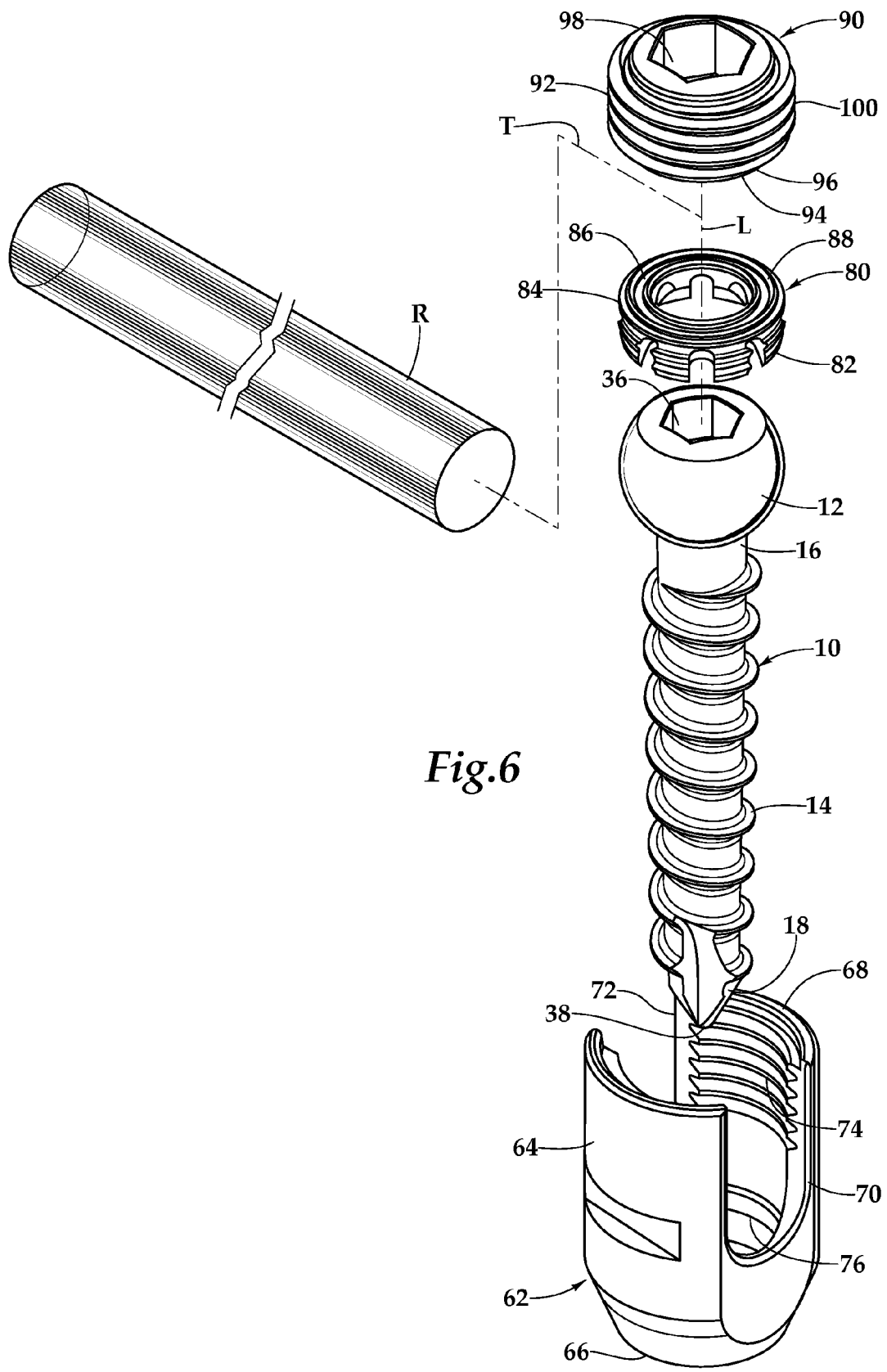
FIG. 6 is a perspective exploded view of the bone screw depicted in FIG. 1 being implemented in a pedicle screw fixation system.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention.

Referring initially to FIGS. 1 through 5, therein is depicted on embodiment of a bone screw 10 having a head 12 that can be adapted to mate with a driver tool, and a shank 14 having proximal and distal ends 16, 18. Three, i.e., first, second, and third, helical threads 20, 22, 24 extend around the shank 14 between the proximal and distal ends 16, 18 thereof. The three helical threads 20, 22, 24 are symmetrically and helically aligned and advance uniformly along the length of the shank 14 for each revolution to define a thread depth that remains constant along the length of the shank 14. The three threads 20, 22, 24 respectively include a first lead 26, a second lead 28, and a third lead 30 such that the three helical leads 26, 28, 30 are offset by approximately 120° from one another.

The head 12 may have a variety of configurations depending on the application. As depicted, the head 12 includes a substantially spherical mating surface 32, with a leveled upper surface 34. A driver-receiving element 36 is formed in the leveled upper surface 34 of the head 12 and is configured to mate to a driver tool for driving the bone screw into bone. In the illustrated embodiment, the substantially spherical head 12 includes a hexagonal socket configured to accept a hex screwdriver. In one implementation, a lower hemisphere of the spherical head presents a deformable face operable for deformation at the mating surface 32.

As discussed, the shank 14 includes the proximal end 16 and the distal end 18 and is particularly adapted to facilitate use of he bone screw 10 in a patients' spinal column or similar structure. The proximal end 16 is integrally connected to the head 12 and a constant diameter may be present from the proximal portion to the distal end 18. A tip 38 is integrally connected to the distal end 18 of the shank 14. The tip 38 may have a variety of configurations. By way of non-limiting examples, the tip 38 may be in the form of a cone-type or gimlet-type tip. As shown, the tip 38 is intersected with a flute to define a self-tapping point. With this arrangement, quick and easy insertion of the bone screw 10 and adequate fixation once implanted are provided.

In one embodiment, the spaced and offset helical threads 20, 22, 24 that extend around and along the shank 14 each begin at the proximal end 16 of the shank and terminate at the distal end 18 of the shank 14. As previously discussed, the helical threads 20, 22, 24 start at a position approximately 120° apart from one another on the shank 14. That is, the three leads 26, 28, 30 are offset by approximately 120° from one another and may be at 0°, 120°, and 240°. The helical threads 20, 22, 24 also have a pitch P that may vary depending upon the requirements of the bone screw. In the illustrated embodiment, the P is approximately 0.1 inches with a pitch angle of approximately 36°. Additionally, as shown, each of the helical threads 20, 22, 24 includes a proximal facing flank 40, a crest 42, and a root 44. Since the helical threads 20, 22, 24 are substantially identical to one another, for purposes of explanation, only single reference numbers are utilized to describe the structure and function of the helical threads 20, 22, 24. The three helical threads may include an angle with the shank 14 of approximately 96°.

Figure 7:
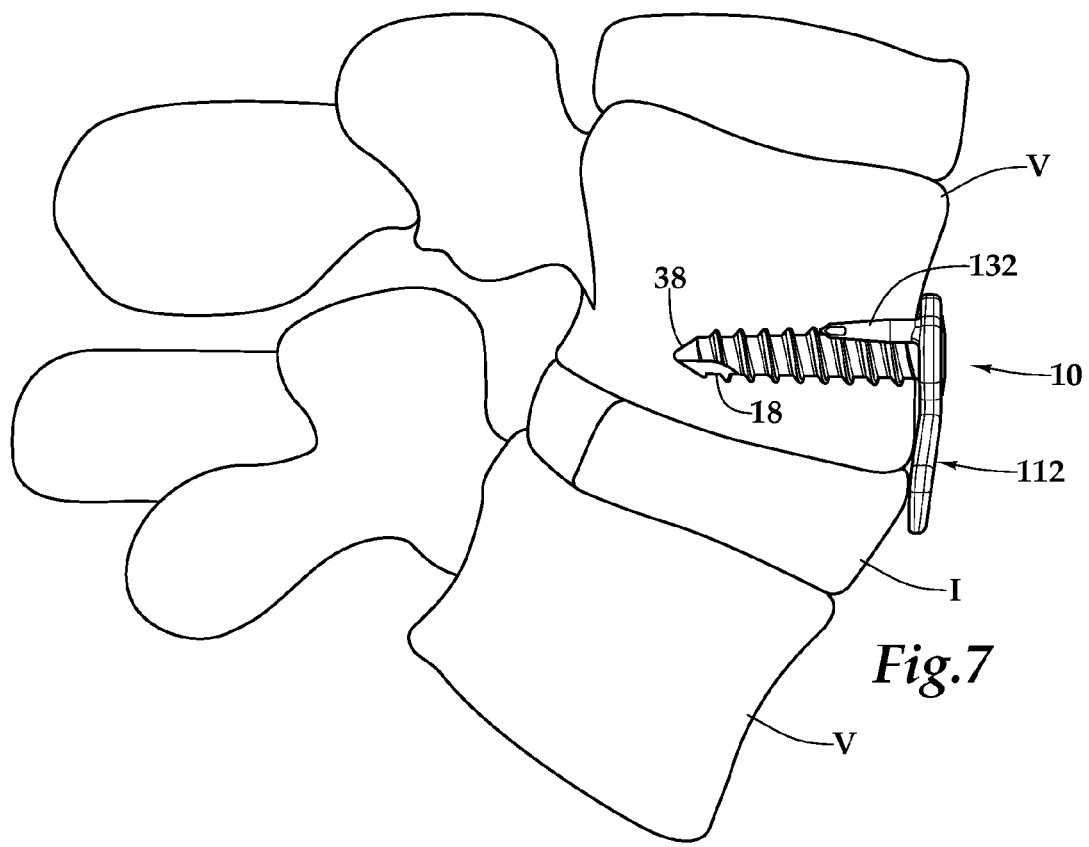
FIG. 7 is a side elevation view of the bone screw depicted in FIG. 1 being implemented with a coupling collar.
Figure 8:
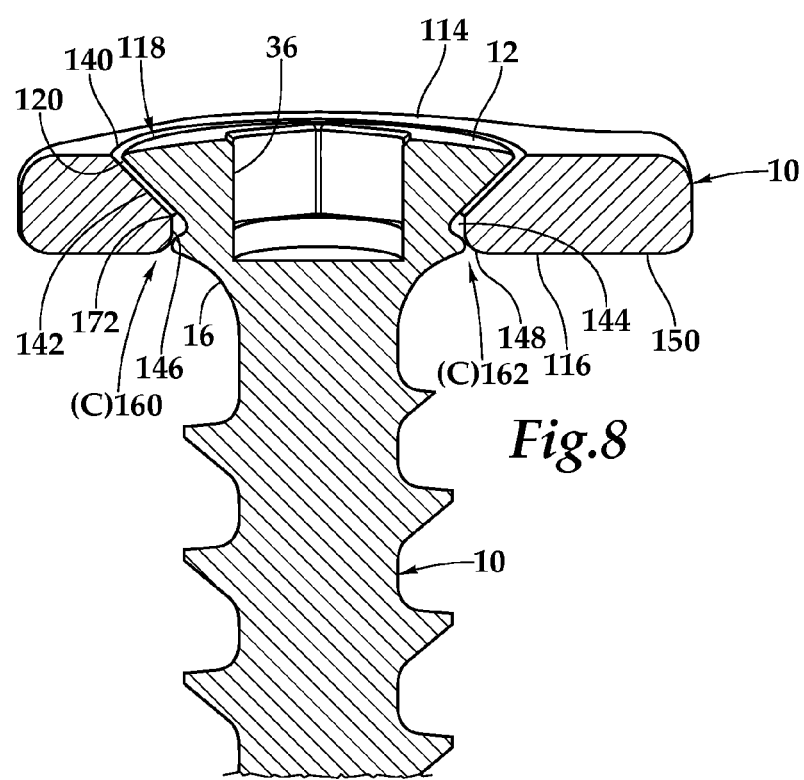
FIG. 8 is a cross-sectional view of a portion of the bone screw and anterior buttress staple of FIG. 7.

It should be appreciated that FIGS. 6-8 illustrate to non-limiting examples of applications of the bone screw presented herein. It will be appreciated that the bone screw will have other fastener applications for the connection of a medical device to bone. Referring now to FIG. 6, therein is depicted one embodiment of a pedicle screw fixation system 60 and rod R utilizing the bone screw 10 presented herein. A pedicle screw 12 includes a threaded shaft 14 and a spherically-shaped head 16 integrally formed therewith at a shank 18. In one implementation, a contact point 20 at the end of the threaded shaft 14 includes an inclined plane. A socket 22 is located on the head of the pedicle screw.

A tulip 62 in the form of a receiving member includes a housing 64 for receiving the bone screw 10 that is defined by a housing bore 66 on one end of a longitudinal axis L and an opening 68 on the other end of the longitudinal axis L. Two opposing U-shaped receiving slots 70, 72 intersect the opening 68 and are aligned along a traverse axis T, which is orthogonal to the longitudinal axis L. Internal threads 74 span the portion of the housing 64 between the receiving slots 70, 72. The bone screw 10 is adapted to be inserted through the opening 68 and the housing bore 66 along the longitudinal axis L of the tulip 62. A spherical-shaped seat 76 is formed proximate to the housing bore 66 to accept the head 12 of the bone screw 10 and provide a universal point of contact having a receiving space thereabout to permit some angular displacement of the tulip 62 about the bone screw 10. In one embodiment, the universal point of contact provides a pivoting linkage for polyaxial placement of the bone screw 10 relative to the tulip 62.

The head 12 of the bone screw 10 is located in contact with the interior of the tulip 62 and, in one embodiment, the shape of the head 12 conforms to the shape of the seat 76.

The pivotal linkage formed between the head 12 and the housing 64 of the tulip 62 provides the rigidity required during surgery to achieve and maintain an accurate placement. This universal joint does not reposition with a minimum or accidental amount of force, rather an intentional amount of force is required for positioning and repositioning. It should be appreciated that although the shape of the head and the shape of the seat 76 are illustrated as being complimentary spherical shapes, other shapes, including conical and pyramidal shapes, for example, are within the teachings presented herein.

A coupling collar 80 that includes a plurality of resilient fingers 82 circumferentially disposed about a body 84. The resilient fingers 82 provide for a snap fit engagement with the head 12 of the pedicle screw 10. A window in the coupling collar extends therethrough to furnish access to the driver-receiving element 36. A deformable face 88 is presented by the coupling collar 80 toward the opening 36. In one embodiment, a pair of collapsible rings create the deformable face 88. The coupling collar 80 not only provides a surface of engagement as will be discussed in further detail below, the coupling collar 80 protects the head 12 and driver-receiving element 36 from damaging torque and force during installation of the pedicle screw fixation system 60.

A driving member or in one specific embodiment, the set screw 90, threadably engages the internal threads 74. A lower end of a body 92 of the set screw 90 presents a deformable face 94 opposite to the deformable face 88 of the coupling collar 80. Three collapsible rings 96 create this second deformable face 94. The upper end of the set screw 90 also includes a socket 98 for accepting the application of torque from a tool, such as an Allen wrench. Additionally, the sides of the set screw include threads 100 that are adapted to mate with the internal threads 42 of the tulip 30.

Although a set screw is depicted, it should be appreciated that the driving member may be any mechanical device that engagingly travels along the longitudinal axis L of the pedicle screw fixation system 60 to apply force or torque to secure or lock the rod. With respect to the coupling collar 80 and the set screw 90, these components are configured to be positioned within the housing 64. Each of the coupling collar 80 and the set screw 90 define respective contact surfaces that are deformable in response to the application of torque and contact between the respective contact surfaces and the rod R. Such application of force increases the surface area of the contact surfaces in contact with the outer surface of the rod R. In one embodiment, as shown, these contact surfaces are smooth. It should be appreciated that these contact surfaces may be roughed, serrated, ribbed, otherwise finished and profiled to improve the engagement between the contact surfaces and the rod R. Similarly, it should be understood that although a smooth rod is depicted, the rod may be correspondingly roughed, serrated, ribbed or otherwise finished and profiled to further improve frictional engagement between the contacts surfaces of the coupling collar 80 and the set screw 90 and the rod R.

Therefore, as shown, in one implementation, the bone screw 10 includes a substantially spherical head 12 having a driver-receiving element formed thereon 36. In this implementation, the spherical head 12 is configured to be held in the tulip 62 and the tulip 62 includes opposing U-shaped receiving slots 70, 72 aligned along a transverse axis. The opposing U-shaped receiving slots 70, 72 are operable for receiving the rod R. An upper hemisphere of the 80 in a snap fit engagement and the lower hemisphere of the spherical head 12 presents a deformable face 88 operable for deformation with the rod R.

Referring to FIGS. 7 and 8, therein is depicted a bone plating system 110, which for purposes of explanation, is depicted as including a bone plate that is schematically illustrated and generally designated 112 and shown as an anterior buttress staple or buttress plate. A bone plate may be a relatively thin metal device which is affixed to bone via screws, such as screw, which, in one implementation, may be any threaded device of metal or other material(s) which is inserted into bone. The bone plate 112 may be used to immobilize bones or bone fragments such that healing can occur. In this respect, the bone screw 10 engages bones in order to immobilize bones or bone fragments or to affix other medical devices, such as metal bone plates, to bones. In particular, the bone plate or the buttress plate 112 in the form of a spinal plate is utilized to support the internal stabilization of adjacent vertebral bodies of a spinal column after replacement of an intervertebral disk, for example. As shown, in one operational embodiment, following insertion of a spinal implant I between vertebrae V, the bone plate 112 is coupled to vertebra V in order to stabilize the vertebrae V and inhibit backout of the spinal implant I from between vertebrae V.

The bone plate 112 may include a "FIG. 8" shaped body having upper and lower body portions 114, 116 each including openings that respectively provide a screw hole 118 and a visualization window 120. The lower body portion 116 further includes a broad span that prevents graft expulsion during use. Additionally, an angle of displacement between the upper body portion 114 and the lower body portion 116 is present to reflect angle of lordosis, such as an angle of cervical lordosis. As will be noted in FIGS. 7 and 8, the head 12 of the bone screw 10 may take different forms depending on the application.

The screw hole 118 located at the upper body portion 114 and extending therethrough from an upper surface to a lower surface accepts the bone screw 10 that is threaded into one of the vertebral bodies, thereby securing the buttress plate 112 and extending the lower body portion 116 over the replaced intervertebral disk. A pair of fangs 132, which provide rotational stability, are located along a lip of the upper body portion 114 and are equally spaced about the screw hole 118. The pair of fangs 132 cooperate with the bone screw 10 to furnish a tripod fixation.

The screw hole 118 includes a counterbore 140 having a beveled surface 142 that intersects, at a pinch point 144, a bore 146 having a conical surface of revolution 148 that transitions into a bone contacting surface 150 of the buttress plate 112. It should be appreciated that the surface of revolution 148 may be of a geometry or curvature other than a conical surface. The counterbore 140 includes three substantially equally rotationally spaced contact regions 160, 162, (third not shown) that align with the sides of an equilateral triangle. Three non-contact regions include three substantially equally rotationally spaced regions that align with a non-linear cross-section of a cylinder. The contact regions and non-contact regions alternate to form a varied surface 172, which has 60°, 120°, 180°, and 240° rotational symmetry and three mirror planes of symmetry. With respect to the bone screw 10, the bone screw 10 is configured to be inserted into bone. A head region 170 includes a proximal root portion 172 which is configured to be secured within the screw hole 118 and an elongated body extends therefrom to the distal end 18 having a point 38.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A bone screw comprising:
   a substantially spherical head having a hexagonal socket configured to accept a hex screwdriver;
   a lower hemisphere of the spherical head presenting a deformable face operable for deformation;
   a shank having a proximal portion and a distal portion with a constant diameter from the proximal portion to the distal portion, the proximal portion being integrally connected to the head; and
   the shank consists of:
      first, second, and third helical threads extending around the shank from the proximal portion to the distal portion, the first, second, and third helical threads being symmetrically and helically aligned, the first, second, and third helical threads advancing uniformly along the length of the shank for each revolution to define a thread depth that remains constant along the length of the shank,
      the first, second, and third helical threads respectively including a first lead, a second lead, and a third lead, the first, second, and third helical leads being offset by approximately 120° from one another,
      the first, second, and third helical threads including a pitch angle of approximately 36°,
      the first, second, and third helical threads including an angle with the shank of approximately 96°,
      a tip integrally connected to the distal portion of the shank, the tip intersected with a flute to define a self-tapping point, and
      the first, second, and third helical threads each comprise proximal and distal flanks that converge toward one another from a root to a crest thereof from the proximal portion to the tip at the distal portion.

2. The bone screw as recited in claim 1, wherein the first, second, and third helical threads comprise a pitch of 0.1 inches.

3. The bone screw as recited in claim 1, wherein the proximal and distal flanks converge toward one another at substantially the same rate.

4. A bone screw comprising:
   a substantially spherical head having a driver-receiving element formed thereon, the spherical head configured to be held in a tulip, the tulip including opposing first and second U-shaped receiving slots aligned along a transverse axis, the opposing first and second U-shaped receiving slots operable for receiving a rod;
   an upper hemisphere of the spherical head configured to accept a coupling collar in a snap fit engagement;
   a lower hemisphere of the spherical head presenting a deformable face operable for deformation with a rod;
   a shank having a proximal portion and a distal portion with a constant diameter from the proximal portion to the distal portion, the proximal portion being integrally connected to the head; and
   the shank consists of:
      first, second, and third helical threads extending around the shank from the proximal portion to the distal portion, the first, second, and third helical threads being symmetrically and helically aligned, the first, second, and third helical threads advancing uniformly along the length of the shank for each revolution to define a thread depth that remains constant along the length of the shank, the first, second, and third helical threads respectively including a first lead, a second lead, and a third lead, the first, second, and third helical leads being offset by approximately 120° from one another, a tip integrally connected to the distal portion of the shank, the tip intersected with a flute to define a self-tapping point, the first, second, and third helical threads each comprise proximal and distal flanks that converge toward one another from a root to a crest thereof, from the proximal portion to the tip at the distal portion, and the proximal and distal flanks converge toward one another at substantially the same rate.

5. The bone screw as recited in claim 4, wherein the first, second, and third helical threads comprise a pitch angle of approximately 36°.

6. The bone screw as recited in claim 4, wherein the first, second, and third helical threads comprise a pitch of 0.1 inches.

* * * * *